United States Patent [19]

Davidson

[11] Patent Number: 5,037,438

[45] Date of Patent: Aug. 6, 1991

[54] ZIRCONIUM OXIDE COATED PROSTHESIS FOR WEAR AND CORROSION RESISTANCE

[75] Inventor: James A. Davidson, Germantown, Tenn.

[73] Assignee: Richards Medical Company, Memphis, Tenn.

[21] Appl. No.: 385,285

[22] Filed: Jul. 25, 1989

[51] Int. Cl.$^5$ .............................................. A61F 2/30
[52] U.S. Cl. ....................................... 623/18; 623/20; 623/22
[58] Field of Search ...................... 623/16, 66, 18, 22, 623/23

[56] References Cited

U.S. PATENT DOCUMENTS

| | | | |
|---|---|---|---|
| 2,987,352 | 6/1961 | Watson | 308/241 |
| 3,643,658 | 2/1972 | Steinemenan | 623/18 |
| 3,677,795 | 7/1972 | Bokros et al. | 623/18 |
| 4,040,129 | 8/1977 | Steinemann et al. | 623/18 |
| 4,145,764 | 3/1979 | Suzuki et al. | 623/16 |
| 4,159,358 | 6/1979 | Hench et al. | 623/16 |
| 4,223,412 | 9/1980 | Aoyagi et al. | 623/16 |
| 4,495,664 | 1/1985 | Blanquaert | 623/23 |
| 4,652,459 | 3/1987 | Engelhardt | 623/18 |
| 4,652,534 | 3/1987 | Kasuga | 433/201.1 |
| 4,671,824 | 6/1987 | Haygarth | 148/6.11 |
| 4,687,487 | 8/1987 | Hintermann | 623/22 |
| 4,728,488 | 3/1988 | Gillett et al. | 316/307 |
| 4,834,756 | 5/1989 | Kenna | 623/16 |

FOREIGN PATENT DOCUMENTS 770080 9/1966 Canada.
1140215 12/1977 Canada.
1325269 7/1971 United Kingdom.

OTHER PUBLICATIONS

Khruschov, "Principles of Abrasive Wear", Wear, 28, 69-88 (1974).
Weightman and Light, "The Effect of the Surface Finish of Alumina and Stainless Steel on the Wear Rate of UHMW Polyethylene", Biomaterials, 7, 20-24 (1986).
Viegas et al., "Metal Materials Biodegration: A Chronoamperometric Study", Journal of Materials Science Materials in Medicine 1, 105-109 (1990).
Briscoe et al., "The Friction and Wear of High Density Polyethylene: The Action of Lead Oxide and Copper Oxide Fillers", Wear, 27, 19-34 (1974).
Rabinowicz, "Lubrication of Metal Surface by Oxide Films", ASLE Translations, 10, 400-407 (1967).
Mäusli et al., "Constitution of Oxides on Titanium Alloys for Surgical Implants", Advances in Bio Materials, 8, 305 (1988).
Rokicki, "The Passive Oxide Film on Electropolished Titanium", (Feb. 1990).
Coll and Jacquot, "Surface Modification of Medical Implants and Surgical Devices Using Tin Layers", Surface and Coatings Technology, 36, 867, (1988).
Bradhurst and Heuer, "The Influence of Oxide Stress on the Breakaway Oxidation of Zircaloy-2", J. Nuclear Materials 37, 35 (1970).
Demizu et al., "Dry Friction of Oxide Ceramics Against Metals: The Effect of Humidity", Tribology Transactions 33, 505 (1990).

(List continued on next page.)

Primary Examiner—David J. Isabella
Attorney, Agent, or Firm—Pravel, Gambrell, Hewitt, Kimball & Krieger

[57] ABSTRACT

Orthopedic implants of zirconium or zirconium-based alloy coated with zirconium oxide to provide low friction, highly wear resistant coatings especially useful in artificial joints, such as hip joints, knee joints, elbows, etc. The invention zirconium oxide coated prostheses are also useful in that the zirconium oxide coatings provide a barrier against implant corrosion caused by ionization of the metal prosthesis. Such protection can be extended by the use of oxidized porous coatings of zirconium or zirconium alloy beads or wire mesh into which bone spicules may grow so that the prosthesis may be integrated into the living skeleton.

21 Claims, 1 Drawing Sheet

OTHER PUBLICATIONS

European Patent Office Search Report: W. German Offenlegungsschrift 2,811,603 to Augsburg–Nurnberg; European Patent Office 0159410 to Sulzer; and W. German Offenlegungsschrift 1,943,801 to Straumann.

Pamphlet, "Zircadyne Corrosion Properties", Teledyne, Wah Chang, Albany, (no date).

Conte, Borello and Cabrini, "Anodic Oxidation of Zircaloy-2", Jnl. of Applied Electrochemistry, vol. 6, pp. 293–299 (1976).

Haygarth and Fenwick, "Improved Wear Resistance of Zirconium by Enhanced Oxide Films", Thin Solid Films, Metallurgical and Protective Coatings, vol. 118, pp. 351–362 (1984).

"The Cementless Fixation of Hip Endoprostheses", edited by Morscher, Mittelmeier, 'Total Hip Replacement with the Autophor Cement-Free Ceramic Prosthesis', pp. 225–241 (1984).

Brown and Merritt, "Evaluation of Corrosion Resistance of Bioloy", Dept. of Biomedical Engineering, Case Western Reserve University, 13 Feb. 1986 (1:8).

Davidson, Schwartz, Lynch, and Gir, "Wear, Creep and Frictional Heating of Femoral Implant Articulating Surfaces and the Effect on Long-Term Performance-Part II, Friction, Heating, and Torque", Jnl. of Biomedical Materials Research: Applied Biomaterials, vol. 22, No. A1, pp. 69–91 (1988).

ASTM F86-84, "Standard Practice for Surface Preparation and Marking of Metallic Surgical Implants", pp. 12–14 (1984), corrected editorially in May 1987.

ZIRCONIUM OXIDE COATED PROSTHESIS FOR WEAR AND CORROSION RESISTANCE

BACKGROUND OF THE INVENTION

1. Field of Invention

This invention relates to metallic orthopedic implants with load bearing surfaces coated with a thin, dense, low friction, highly wear-resistant coating of zirconium oxide, nitride, carbide or carbonitride. This coating is especially useful on the portions of these prostheses which bear against surfaces which are subject to high rates of wear. An example is the femoral head of a hip-stem prosthesis which engages a counter-bearing surface in an acetabular cup which is often made of a softer material such as ultra-high molecular weight polyethylene.

The invention also relates to zirconium oxide coatings on the non-load bearing surfaces of an orthopedic implant where the zirconium oxide provides a barrier between the metallic prosthesis and body tissue thereby preventing the release of metal ions and corrosion of the implant. Additionally, this oxidation process and the associated increase in surface oxygen content and hardness increases the strength of the metal substrate and improves the fatigue properties of the implant.

2. Background

Orthopedic implant materials must combine high strength, corrosion resistance and tissue compatibility. The longevity of the implant is of prime importance especially if the recipient is relatively young because it is desirable that the implant should function for the complete lifetime of a patient. Because certain metal alloys have the required mechanical strength and biocompatibility, they are ideal candidates for the fabrication of prostheses. 316L stainless steel, chrome-cobalt-molybdenum alloys and more recently titanium alloys have proven to be the most suitable materials for the fabrication of load-bearing prostheses.

One of the variables affecting the longevity of load-bearing implants such as hip-joint implants is the rate of wear of the articulating surfaces and long-term effects of metal ion release. A typical hip-joint prosthesis includes a stem, a femoral head and an acetabular cup against which the femoral head articulates. Wear of either or both of the articulating surfaces results in an increasing level of wear particulates and "play" between the femoral head and the cup against which it articulates. Wear debris can contribute to adverse tissue reaction leading to bone resorption, and ultimately the joint must be replaced.

The rate of wear of the acetabular cup and the femoral head surfaces is dependent upon a number of factors which include the relative hardness and surface finish of the materials which constitute the femoral head and the acetabular cup, the frictional coefficient between the materials of the cup and head, the load applied and the stresses generated at the articulating surfaces. The most common material combinations currently used in the fabrication of hip-joint implants include femoral heads of cobalt or titanium alloys articulating against acetabular cups lined with organic polymers or composites of such polymers including, for instance, ultra-high molecular weight polyethylene and femoral heads of polished alumina in combination with acetabular cups lined with an organic polymer or composite or made of polished alumina.

Of the factors which influence the rate of wear of conventional hip-joint implants, the most significant are patient weight and activity level Additionally, heat which is generated by friction in the normal use of the implant as, for instance, in walking has been shown to cause accelerated creep and wear of the polyethylene cup. Furthermore, there is a correlation between the frictional moment which transfers torque loading to the cup and the frictional coefficient between the femoral head and the surface of the acetabular cup against which the head articulates. Cup torque has been associated with cup loosening. Thus, in general, the higher the coefficient of friction for a given load, the higher the level of torque generated. Ceramic bearing surfaces have been shown to produce significantly lower levels of frictional torque.

It is also noteworthy that two of the three commonly used hip-joint systems as indicated above include a metallic femoral head articulating against a UHMWPE liner inside the acetabular cup. UHMWPE, being a polymeric material, is more susceptible to creep when heated than the commonly used metal alloys or ceramics and is consequently more susceptible to wear than the alloys or ceramics.

It has also been found that metal prostheses are not completely inert in the body. Body fluids act upon the metals causing them to slowly corrode by an ionization process thereby releasing metal ions into the body. Metal ion release from the prosthesis is also related to the articulation and rate of wear of load bearing surfaces because, as may be expected, when a metallic femoral head, for instance, is articulated against UHMWPE, the passive oxide film which forms on the femoral head is constantly removed. The repassivation process constantly releases metal ions during this process. Furthermore, the presence of third-body wear (cement or bone debris) accelerates this process and micro fretted metal particles can increase friction. Consequently, the UHMWPE liner inside the acetabular cup, against which the femoral head articulates, is subjected to accelerated levels of creep, wear, and torque.

U.S. Pat. No. 4,145,764 to Suzuki et al recognized that while metal prostheses have excellent mechanical strength they tend to corrode in the body by ionization. Suzuki et al also recognized the affinity between ceramics and bone tissue, but noted that ceramic prostheses are weak on impact resistance. Suzuki et al therefore proposed a metal prosthesis plasma sprayed with a bonding agent which is in turn covered with a porous ceramic coating which would allow the ingrowth of bone spicules into the pores. This combination, it was said, would provide both the mechanical strength of metals and the biocompatibility of ceramics.

The Suzuki patent did not address the issue of friction or wear of orthopedic implant bearing surfaces but confined itself to the single issue of the biocompatibility of metal prostheses. Furthermore, Suzuki et al did not address the issue of dimensional changes that occur when applying a coating or the effect of these dimensional changes in the tightness of fit between the surfaces of an articulating joint prosthesis.

In addition, the application of ceramic coatings to metal substrates often results in non-uniform, poorly-bonded coatings which tend to crack due to the differences in thermal expansion between the ceramic and the underlying metal substrate. Furthermore, such coatings are relatively thick (50-300 microns) and since the bond between the metal and the ceramic coating is often weak there is always the risk of galling or separation of the ceramic coating.

U.S. Pat. No. 3,677,795 to Bokros is directed to the application of a carbide coating over a metallic prosthetic device. This method of forming the carbide coating requires that the prosthesis be heated to temperatures of at least about 1350° C. in a reaction chamber through which a hydrocarbon gas such as propane or butane flows. The method is said to produce a prosthetic device which has "excellent compatibility with body tissue and is non-thrombogenic." Bokros does not address the issues of friction, heating, creep and wear of orthopedic implant bearing surfaces, or changes induced in the mechanical properties of the underlying metal due to this high-temperature treatment.

There exists a need for a metal alloy-based orthopedic implant having low friction, highly wear resistant load bearing surfaces which may be implanted for the lifetime of the recipient. There also exists a need for a metal alloy-based orthopedic implant that is not prone to corrosion by the action of body fluids so that it is biocompatible and stable over the lifetime of the recipient.

SUMMARY OF THE INVENTION

The invention provides a zirconium or zirconium-containing metal alloy prosthesis coated via in situ oxidation with zirconium oxide. The zirconium oxide coating provides the invention prosthesis with a thin, dense, low friction, wear resistant, biocompatible surface ideally suited for use on articulating surfaces of joint prostheses wherein a surface or surfaces of the joint articulates, translates or rotates against mating joint surfaces. The zirconium oxide coating may therefore be usefully employed on the femoral heads or inside surfaces of acetabular cups of hip-joint implants or on the articulating surfaces of other types of prostheses, such as knee joints.

When a zirconium oxide-coated joint surface is employed in a manner wherein it articulates or rotates against a non-metallic or non-zirconium oxide coated surface, the low friction characteristic of the coating causes reduced friction, wear, and heat generation relative to prior art prostheses. This reduced heat generation results in a lowered tendency for the non-metallic or non-zirconium oxide coating bearing surface to experience creep and torque so that the useful life of the opposing surface is enhanced. Thus, for instance, where the zirconium oxide coated femoral head of a hip joint implant articulates against an opposing ultra-high molecular weight polyethylene (UHMWPE) surface liner of an acetabular cup, friction and wear is reduced so that the UHMWPE is subjected to lower levels of torque, wear, and heat generation and consequently experiences lowered levels of creep and cup loosening resulting in an enhancement of the life of the liner and the prosthesis.

The zirconium oxide coating of the subject invention is also useful in providing a biocompatible, inert ceramic barrier between the zirconium-containing metal alloy-based prosthesis and body fluids. Thus, since the zirconium oxide surface is not prone to ionization and wear-induced corrosion, both the life span and the biocompatibility of the prosthesis are enhanced.

Additionally, the natural in situ formation of a zirconium oxide coating from the presence of zirconium in the substrate metal involves oxygen diffusion into the metal substrate below the oxide coating. Oxygen, an alloying constituent in zirconium, increases the strength of the metal substrate, particularly the fatigue strength. Resistance to fatigue loading is paramount in many orthopedic implant applications such as the hip stem, and femoral and tibial knee components. Thus, not only does the formation of the zirconium oxide coating improve wear, friction, and corrosion resistance, it also improves the mechanical integrity of the implant device from a strength standpoint.

DETAILED DESCRIPTION OF THE PREFERRED EMBODIMENTS

One aspect of the invention is to provide low friction, wear resistant coatings on the articulating surfaces of prosthetic devices. Illustrative examples of such articulating surfaces are shown in the schematic diagrams, FIGS. 1-4.

Figure 1:
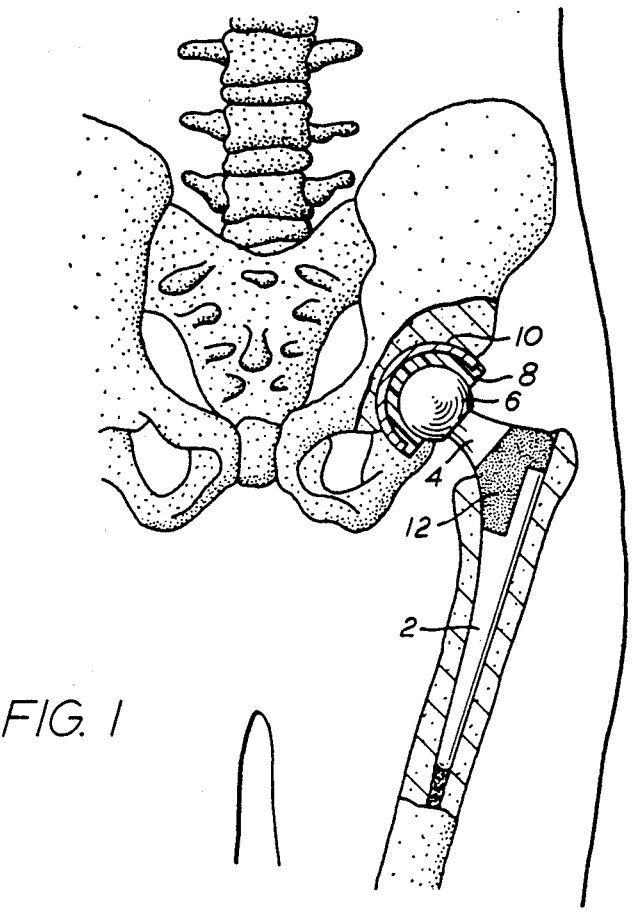
FIG. 1 is a schematic diagram depicting a hip joint prosthesis in position.
Figure 2:
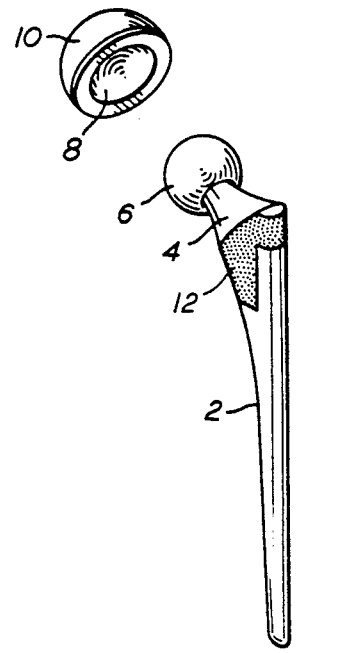
FIG. 2 is a schematic diagram showing a typical hip joint prosthesis.

A typical hip joint assembly is shown in situ in FIG. 1. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to allow stabilization of the implant by ingrowth of surrounding tissue into the porous coating. Similarly, such a coating can also be applied to the acetabular component. The femoral head 6 may be an integral part of the hip joint stem 2 or may be a separate component mounted upon a conical taper at the end of the neck 4 of the hip joint prosthesis. This allows the fabrication of a prosthesis having a metallic stem and neck but a femoral head of some other material, such as ceramic. This method of construction is often desirable because ceramics have been found to generate less frictional torque and wear when articulating against the UHMWPE lining of an acetabular cup. Additionally, zirconia ceramic has been shown to produce less wear of the UHMWPE than alumina. Regardless of the materials, however, the femoral head articulates against the inner surface of the acetabular cup thereby causing wear and, in the long term, this may necessitate prosthesis replacement. This is especially the case where the femoral head is of metal and the acetabular cup is lined with an organic polymer or composite thereof. While these polymeric surfaces provide good, relatively low friction surfaces and are biocompatible, they are, as explained above, subject to wear and accelerated creep due to the frictional heat and torque to which they are subjected during ordinary use.

Figure 3:
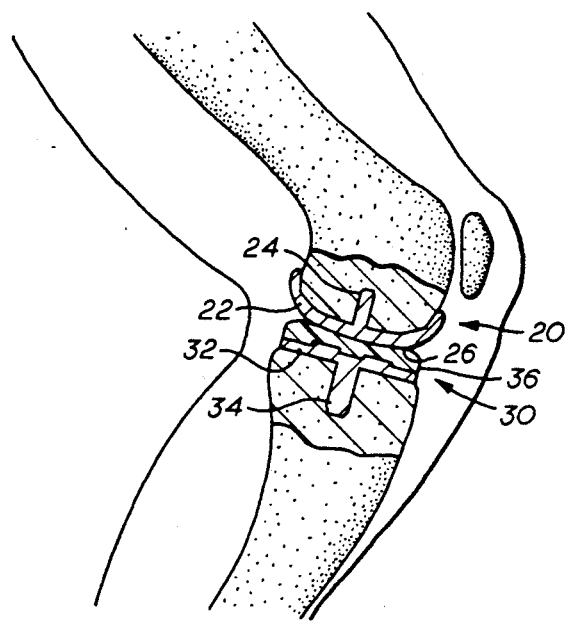
FIG. 3 is a schematic diagram of a knee joint prosthesis in place.
Figure 4:
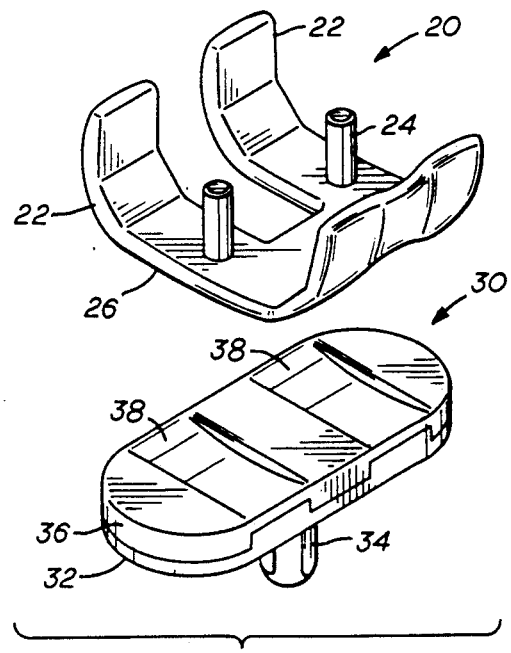
FIG. 4 is a schematic diagram of the parts of a typical knee joint.

A typical knee joint prosthesis is shown in situ in FIG. 3. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. While condyles are typically fabricated of metals, the tibial platform may be made from an organic polymer or a polymer-based composite. Thus, the hard metallic condyle surfaces 26 would articulate against a relatively softer organic composition. As previously explained, this may result in wear of the organic material, i.e. the tibial platform necessitating the replacement of the prosthesis. As in the case of the hip joint, porous bead or wire mesh coatings can also be applied to either the tibial or femoral components of the knee or both.

The invention provides zirconium oxide coated orthopedic implants or prostheses fabricated of zirconium or zirconium containing metal alloys or a thin coating of zirconium or zirconium alloy on conventional orthopedic implant materials. In order to form continuous and useful zirconium oxide coatings over the desired surface of the metal alloy prosthesis substrate, the metal alloy should contain from about 80 to about 100 wt. % zirconium, preferably from about 95 to about 100 wt. %. Oxygen, niobium, and titanium include common alloying elements in the alloy with often times the presence of hafnium. Yttrium may also be alloyed with the zirconium to enhance the formation of a tougher, yttria-stabilized zirconium oxide coating during the oxidation of the alloy. While such zirconium containing alloys may be custom formulated by conventional methods known in the art of metallurgy, a number of suitable alloys are commercially available. These commercial alloys include among others Zircadyne 705, Zircadyne 702, and Zircalloy.

The base zirconium containing metal alloys are cast or machined by conventional methods to the shape and size desired to obtain a prosthesis substrate. The substrate is then subjected to process conditions which cause the natural (in situ) formation of a tightly adhered, diffusion-bonded coating of zirconium oxide on its surface. The process conditions include, for instance, air, steam, or water oxidation or oxidation in a salt bath. These processes ideally provide a thin, hard, dense, blue-black or black, low-friction wear-resistant zirconium oxide film or coating of thicknesses typically on the order of several microns ($10^6$ meters) on the surface of the prosthesis substrate. Below this coating, diffused oxygen from the oxidation process increases the hardness and strength of the underlying substrate metal.

The air, steam and water oxidation processes are described in now-expired U.S. Pat. No. 2,987,352 to Watson, the teachings of which are incorporated by reference as though fully set forth. The air oxidation process provides a firmly adherent black or blue-black layer of zirconium oxide of highly oriented monoclinic crystalline form. If the oxidation process is continued to excess, the coating will whiten and separate from the metal substrate. The oxidation step may be conducted in either air, steam or hot water. For convenience, the metal prosthesis substrate may be placed in a furnace having an oxygen-containing atmosphere (such as air) and typically heated at 700°-1100° F. up to about 6 hours. However, other combinations of temperature and time are possible. When higher temperatures are employed, the oxidation time should be reduced to avoid the formation of the white oxide.

It is preferred that a blue-black zirconium oxide layer ranging in thickness from about 1 to about 5 microns should be formed. For example, furnace air oxidation at 1000° F. for 3 hours will form an oxide coating on Zircadyne 705 about 4–5 microns thick. Longer oxidation times and higher oxidation temperatures will increase this thickness, but may compromise coating integrity. For example, one hour at 1300° F. will form an oxide coating about 14 microns in thickness, while 21 hours at 1000° F. will form an oxide coating thickness of about 9 microns. Of course, because only a thin oxide is necessary on the surface, only very small dimensional changes, typically less than 10 microns over the thickness of the prosthesis, will result. In general, thinner coatings (1–4 microns) have better attachment strength.

One of the salt-bath methods that may be used to apply the zirconium oxide coatings to the metal alloy prosthesis, is the method of U.S. Pat. No. 4,671,824 to Haygarth, the teachings of which are incorporated by reference as though fully set forth. The salt-bath method provides a similar, slightly more abrasion resistant blue-black or black zirconium oxide coating. The method requires the presence of an oxidation compound capable of oxidizing zirconium in a molten salt bath. The molten salts include chlorides, nitrates, cyanides, and the like. The oxidation compound, sodium carbonate, is present in small quantities, up to about 5 wt. %. The addition of sodium carbonate lowers the melting point of the salt. As in air oxidation, the rate of oxidation is proportional to the temperature of the molten salt bath and the '824 patent prefers the range 550°–800° C. (1022°–1470° C.). However, the lower oxygen levels in the bath produce thinner coatings than for furnace air oxidation at the same time and temperature. A salt bath treatment at 1290° F. for four hours produces an oxide coating thickness of roughly 7 microns.

Whether air oxidation in a furnace or salt bath oxidation is used, the zirconium oxide coatings are quite similar in hardness. For example, if the surface of a wrought Zircadyne 705 (Zr, 2–3 wt. % Nb) prosthesis substrate is oxidized, the hardness of the surface shows a dramatic increase over the 200 Knoop hardness of the original metal surface. The surface hardness of the blue-black zirconium oxide surface following oxidation by either the salt bath or air oxidation process is approximately 1700-2000 Knoop hardness.

These diffusion-bonded, low friction, highly wear resistant zirconium oxide coatings are applied to the surfaces of orthopedic implants subject to conditions of wear. Such surfaces include the articulating surfaces of knee joints, elbows and hip joints. As mentioned before, in the case of hip joints, the femoral head and stem are typically fabricated of metal alloys while the acetabular cup may be fabricated from ceramics, metals or organic polymer-lined metals or ceramics.

When the zirconium oxide coated femoral head is used in conjunction with any of these acetabular cups, the coefficient of friction between the femoral head and the inner surface of the cup is reduced so that less heat and torque is generated and less wear of the mating bearing surface results. This reduction in heat generation, frictional torque, and wear is particularly important in the case of acetabular cups lined with organic polymers or composites of such polymers. Organic polymers, such as UHMWPE, exhibit rapidly increased rates of creep when subjected to heat with consequent deleterious effect on the life span of the liner. Wear debris of the polymer leads to adverse tissue response and loosening of the device. Thus, not only does the zirconium oxide coating serve to protect the prosthesis substrate to which it is applied and increase its mechanical strength properties but, as a result of its low friction surface, it also protects those surfaces against which it is in operable contact and consequently enhances the performance and life of the prosthesis.

The usefulness of zirconium oxide coated prosthesis is not limited to load bearing prostheses, especially joints, where a high rate of wear may be encountered. Because the zirconium oxide coating is firmly bonded to the zirconium alloy prosthesis substrate, it provides a barrier between the body fluids and the zirconium alloy metal thereby preventing the corrosion of the alloy by the process of ionization and its associated metal ion release.

Oxygen diffusion into the metal substrate during oxidation also increases the strength of the metal. Consequently, a zirconium oxide coated prosthesis may be expected to have a greater useful service life.

Zirconium or zirconium alloy can also be used to provide a porous bead or wire mesh surface to which surrounding bone or other tissue may integrate to stabilize the prosthesis. These porous coatings can be treated simultaneously by the oxidation treatment in a manner similar to the oxidation of the base prosthesis for the elimination or reduction of metal ion release. Furthermore, zirconium or zirconium alloy can also be used as a surface layer applied over conventional implant materials prior to in situ oxidation and formation of the zirconium oxide coating.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

I claim:

1. A prosthesis for implantation in a patient, comprising:
   (a) a prosthesis body formed of zirconium or zirconium alloy comprising an implant portion for inserting into the body tissue of the patient;
   (b) a bearing surface comprising at least one condyle on the prosthesis body;
   (c) a tibial component formed of an organic polymer or polymer-based composite and adapted to cooperate with the bearing surface; and
   (d) a thin coating of blue-black or black zirconium oxide directly on the bearing surface of the condyle portion for reducing wear of the organic polymer or polymer-based composite tibial component.

2. The prosthesis of claim 1 wherein said thin blue-black or black zirconium oxide coating is from about 1 to about 5 microns thick.

3. The prosthesis of claim 2 wherein the implant portion of the prothesis body further comprises an irregular surface structure adapted to accommodate tissue ingrowth on a portion of the prosthesis body.

4. The prosthesis of claim 3 wherein the irregular surface structure is formed of zirconium or zirconium alloy beads attached to the outer surface of the prosthesis body, wherein at least a portion of the surface of the beads is oxidized to blue-black or black zirconium oxide.

5. The prosthesis of claim 3 wherein the irregular surface structure is formed of zirconium or zirconium alloy wire mesh connected to the outer surface of the prosthesis body, wherein at least a portion of the surface of the mesh is oxidized to blue-black or black zirconium oxide.

6. A prosthesis for implantation in a patient, comprising:
   (a) a hip prosthesis body for implantation into a femor comprising a head portion formed of zirconium or zirconium alloy;
   (b) a bearing surface on the head portion of the prosthesis body;
   (c) an acetabular cup having an inner surface formed of an organic polymer or a polymer-based composite, said inner surface being adapted to cooperate with the bearing surface on the head portion; and
   (d) a thin coating of blue-black or black zirconium oxide directly on the bearing surface of the head portion for reducing wear of the acetabular cup inner surface.

7. The prosthesis of claim 6 wherein said thin blue-black or black zirconium oxide coating is from about 1 to about 5 microns thick.

8. The prosthesis of claim 6 wherein the prosthesis body further comprises an irregular surface structure adapted to accommodate tissue ingrowth on a portion of the prosthesis body.

9. The prosthesis of claim 8 wherein the irregular surface structure is formed of zirconium or zirconium alloy beads connected to the outer surface of the prosthesis body, wherein at least a portion of the surface of the beads is oxidized to blue-black or black zirconium oxide.

10. The prosthesis of claim 8 wherein the irregular surface structure is formed of zirconium or zirconium alloy wire mesh connected to the outer surface of the prosthesis body, wherein at least a portion of the surface of the mesh is oxidized to blue-black or black zirconium oxide.

11. A prosthesis for implantation in a patient, comprising:
    (a) a prosthesis body formed of zirconium or zirconium alloy comprising an implant portion for insertion into the body tissue of the patient;
    (b) a bearing surface on the prosthesis body, the bearing surface being sized and shaped to engage or cooperate with a second bearing surface on another prosthesis portion, said second bearing surface being formed of an organic polymer or polymer-based composite; and
    (c) a coating of blue-black or black zirconium oxide from about 1 to about 5 microns in thickness on the bearing surface of the prosthesis body for reducing wear on the organic polymer or polymer-based second bearing surface of said another prosthesis portion.

12. The prosthesis of claim 11 wherein the prosthesis body is a hip joint having a head portion as a bearing surface and wherein said another prosthesis portion is an acetabular cup, said head portion being adapted to cooperate with the inner surface of the acetabular cup, said inner surface comprising an organic polymer or polymer-based composite.

13. The prosthesis of claim 11 wherein the prosthesis body is a knee joint and the bearing surface of the prosthesis body comprises at least one condyle, and wherein said another prosthesis portion comprises a tibial component formed of an organic polymer or polymer-based composite, said at least one condyle being adapted to cooperate with the tibial component.

14. The prosthesis of claim 11 wherein the prosthesis body further comprises an irregular surface structure adapted to accommodate tissue in growth on a portion of the prosthesis body.

15. The prosthesis of claim 14 wherein the irregular surface structure is formed of zirconium or zirconium alloy beads connected to the outer surface of the prosthesis body, wherein at least a portion of the surface of the beads is oxidized to blue-black or black zirconium oxide.

16. The prosthesis of claim 14 wherein the irregular surface structure is formed of zirconium or zirconium alloy wire mesh connected to the outer surface of the prosthesis body, wherein at least a portion of the surface of the mesh is oxidized to blue-black or black zirconium oxide.

17. A prosthesis for implantation in a patient, comprising:
(a) a prosthesis body formed of zirconium or zirconium alloy comprising an implant portion for inserting into the body tissue of the patient;
(b) a bearing surface on the prosthesis body;
(c) a counter-bearing surface formed of an organic polymer or polymer-based composite and adapted to cooperate with the bearing surface; and
(d) a thin coating of blue-black or black zirconium oxide directly on the bearing surface for reducing wear of the organic polymer or polymer-based composite counter-bearing surface.

18. The prosthesis of claim 17 wherein said thin blue-black or black zirconium oxide coating is from about 1 to about 5 microns thick.

19. The prosthesis of claim 18 wherein the implant portion of the prothesis body further comprises an irregular surface structure adapted to accommodate tissue ingrowth on a portion of the prosthesis body.

20. The prosthesis of claim 19 wherein the irregular surface structure is formed of zirconium or zirconium alloy beads attached to the outer surface of the prosthesis body, wherein at least a portion of the surface of the beads is oxidized to blue-black or black zirconium oxide.

21. The prosthesis of claim 19 wherein the irregular surface structure is formed of zirconium or zirconium alloy wire mesh connected to the outer surface of the prosthesis body, wherein at least a portion of the surface of the mesh is oxidized to blue-black or black zirconium oxide.

* * * * *